(12) United States Patent
Schoeniger et al.

(10) Patent No.: US 10,267,788 B1
(45) Date of Patent: Apr. 23, 2019

(54) LINEAR PEPTIDES THAT MIMIC STRUCTURAL EPITOPES FOR ANTIBODY ASSAYS

(71) Applicant: National Technology & Engineering Solutions of Sandia, LLC, Albuquerque, NM (US)

(72) Inventors: Joseph S. Schoeniger, Oakland, CA (US); Peter Anderson, Bothell, WA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 727 days.

(21) Appl. No.: 14/159,308

(22) Filed: Jan. 20, 2014

Related U.S. Application Data

(60) Provisional application No. 61/759,494, filed on Feb. 1, 2013.

(51) Int. Cl.
*G01N 33/531* (2006.01)
*C07K 14/005* (2006.01)

(52) U.S. Cl.
CPC ......... *G01N 33/531* (2013.01); *C07K 14/005* (2013.01)

(58) Field of Classification Search
CPC .................................................. G01N 33/531
See application file for complete search history.

(56) References Cited

U.S. PATENT DOCUMENTS

2006/0073518 A1\* 4/2006 Timmerman ........... C40B 30/04
435/7.1

OTHER PUBLICATIONS

Chakraborty et al. (Biochem. J. (2005) 390, 573-581).\*
Vanhoorelbeke et al. (J. Biol. Chem., 2003, 278(39):37815-37821).\*
Barany et al. (Int. J. Peptide Res., 1987, 30:705-739) (Year: 1987).\*
Schafmeister, C. E., et al., "An all-hydrocarbon cross-linking system for enhancing the helicity and metabolic stability of peptides", J. Am. Chem. Soc., 122, (2000), pp. 5891-5892.

\* cited by examiner

*Primary Examiner* — Jeremy C Flinders
(74) *Attorney, Agent, or Firm* — Madelynne J. Farber

(57) ABSTRACT

A method including identifying one or more structures in adjacent sequences of one or more proteins that can be mimicked by a peptide; and assembling a peptide that mimics the one or more secondary structures. A method including assembling epitopes of linked pairs of discontiguous peptide subsequences that mimic one or more structures in sequences of a protein; and assaying antibodies against the epitopes.

9 Claims, 4 Drawing Sheets

LINEAR PEPTIDES THAT MIMIC STRUCTURAL EPITOPES FOR ANTIBODY ASSAYS

CROSS-REFERENCE TO RELATED APPLICATION

This application claims the benefit of the earlier filing date of U.S. Provisional Patent Application No. 61/759,494, filed Feb. 1, 2013 entitled "Linear Peptides that Mimic Structural Epitopes for Antibody Assays." The aforementioned application is hereby incorporated by reference, in its entirety, for all purposes.

STATEMENT OF GOVERNMENT RIGHTS

This invention was developed under Contract DE-AC04-94AL85000 between Sandia Corporation and the U.S. Department of Energy. The U.S. Government has certain rights in this invention.

FIELD

Protein mimics.

BACKGROUND

Medical diagnostic assays often measure levels of antibodies against various proteins. Arrays of peptides may be used to simultaneously assay many different antibodies. But most antibodies bind to sequence-discontiguous structural epitopes.

Measurements of antibody (Ab) levels in blood and other tissues are widely used for screening and diagnosis of infectious diseases and many other medical conditions. Such tests may be used for public health screening or as part of a biodefense response architecture. The immune system produces antibodies (Abs) each with selective binding to particular proteins (or other biomolecules) called antigens. Abs are themselves proteins, and may be specified by their sequence. Each such specific Ab that is part of an effective immune response to a protein target antigen recognizes a particular epitope, a part of the target protein structure, typically on the exposed surface of the protein. The target proteins are themselves linear polypeptides, but they are folded into complex structures and may form complexes with other polypeptide chains. Epitopes may consist of extended linear stretches of the target protein sequence, but more often are composed of spatially adjacent discontiguous subsequences of the target protein or target protein complex, each subsequence a few amino acids in length (e.g., five amino acid residues). These spatially adjacent discontiguous subsequences are referred to as structural epitopes, as opposed to the less common extended linear epitopes.

In order to quickly and cheaply assay a single sample (e.g., assaying a blood sample for Abs against multiple different pathogens, as one would want to when screening people for exposure after a putative biological weapons attack) various formats may be used to simultaneously screen for binding of Abs to many different antigens. One format is an array of immobilized protein antigens, each antigen in a small spot in unique location in the array, so that reading out the location of antibody binding events allows the antibody binding specificity profile to be assessed (e.g., thus, in the example above, the target organism). Such protein arrays are costly, have limited chemical and thermal stability. Also, proteins may not be sufficiently densely immobilized or present the correct epitope structure, decreasing their sensitivity.

An alternative to protein arrays is to use arrays of short linear peptides. Compared to protein antigens, these are more chemically stable and less expensive, if they are relatively short (i.e., less than 20 amino acid residues). Such peptides may be immobilized or synthesized in situ at high density with extremely high sequence diversity: arrays may have >1 million different sequences. Various experimental and computational strategies may be used to select the peptide sequences, including purely random sequences, followed by purely empirical characterization of Ab binding profiles of various serotypes. However, it is desirable to find a design procedure that exploits the extensive genomics-based knowledge of actual or putative target protein sequences. (The combinatorial diversity of peptides is such that no chip however large will ever by able to comprehensively sample it). For example, one procedure is to simply take all short (e.g., 15 amino acid long) subsequences from each antigen protein and synthesize the corresponding peptides for use on chip.

One problem with using short linear subsequences of peptide arrays is that most epitopes are not linear subsequences, and the physical size of the binding site on the Ab molecule is such that it generally cannot contact more than a few amino acids of a peptide in extended conformation. Because Abs that recognize protein antigens generally recognize protein structures composed of co-localized but discontiguous patches of amino acid sequence (see above) linear peptides "tiled" from the protein sequence generally will not fully occupy the Ab binding site, leading to weaker binding of the Ab to the peptide compared to the protein epitope.

SUMMARY

Peptides and a method for identifying and generating (e.g., deriving, synthesizing) a peptide that can effectively mimic the structure of protein or proteins (e.g., proteins of a protein complex) in a way that is useful for diagnostic or vaccine purposes are described. Representatively, in one embodiment, such peptides can effectively mimic structural epitopes to assist in the assay of antibodies.

BRIEF DESCRIPTION OF THE DRAWINGS

The invention may best be understood by referring to the following description and accompanying drawings that are used to illustrate embodiments of the invention. In the drawings.

DETAILED DESCRIPTION

In general, there are certain segments of protein structures that can be replicated or mimicked by short sequences of amino acid residues (peptides). For example, where a protein displays a beta sheet secondary structure of parallel or anti-parallel beta strands (polypeptide sequences) linked by a short loop (e.g., β hairpin) of two to five amino acid residues, a peptide of, for example, the subsequences of amino acids of the adjacent strands as well as the β hairpin may mimic a function or property of that portion of the protein or proteins. As noted above, antigens often contain epitopes of spatially adjacent discontiguous subsequences each of a few amino acid residues in length, for example, two adjacent β hairpins. In one embodiment, a peptide can be formed of the same or similar subsequences and be made complementary to a shape recognized by an antibody. Accordingly, in such embodiment, the peptide can mimic a structural epitope of a protein.

As described herein, such subsequences that define a peptide mimic generally include two to less than 10 amino acid residues from or corresponding to each of the adjacent sequences. In another embodiment, the amino acid residues of each subsequence of a peptide mimic is seven amino acid residues or less. In another embodiment, the number of amino acid residues of each subsequence is five amino acid residues or less (e.g., two amino acid residues to four amino acid residues). The peptide mimic composed of the amino acid residues of the adjacent sequences or chains, in one embodiment, is linked with a linker of amino acid residues. In one embodiment, the linker of amino acid residues is less than five amino acid residues. In this manner, by linking adjacent subsequences, the end of the subsequences are joined to form, for example, a contiguous structure from which a three dimensional structure of the protein or adjacent proteins may be impersonated or mimicked. For example, where the three dimensional structure is two adjacent β hairpins in a protein, induced by flanking portions of the protein chain forming antiparallel B strands, the spatially adjacent pair of β hairpins is mimicked in the constructed peptide. In one embodiment, in addition to linking the subsequences (residues of adjacent peptides), for example, at one end, the subsequences may be cross-linked to assist in the maintenance of a three dimensional structure. The cross-linking tends to confine the peptide structure and thus reduce its entropy. Modifications to the peptide in addition to cross-linking or as a substitute for cross-linking include covalent modifications commonly found in natural epitopes such as glycosylation or phosphorylation, or synthetic covalent or non-covalent modifications that enhance the ability of the peptide to render a desired shape or enhance its chemical stability.

Figure 1:
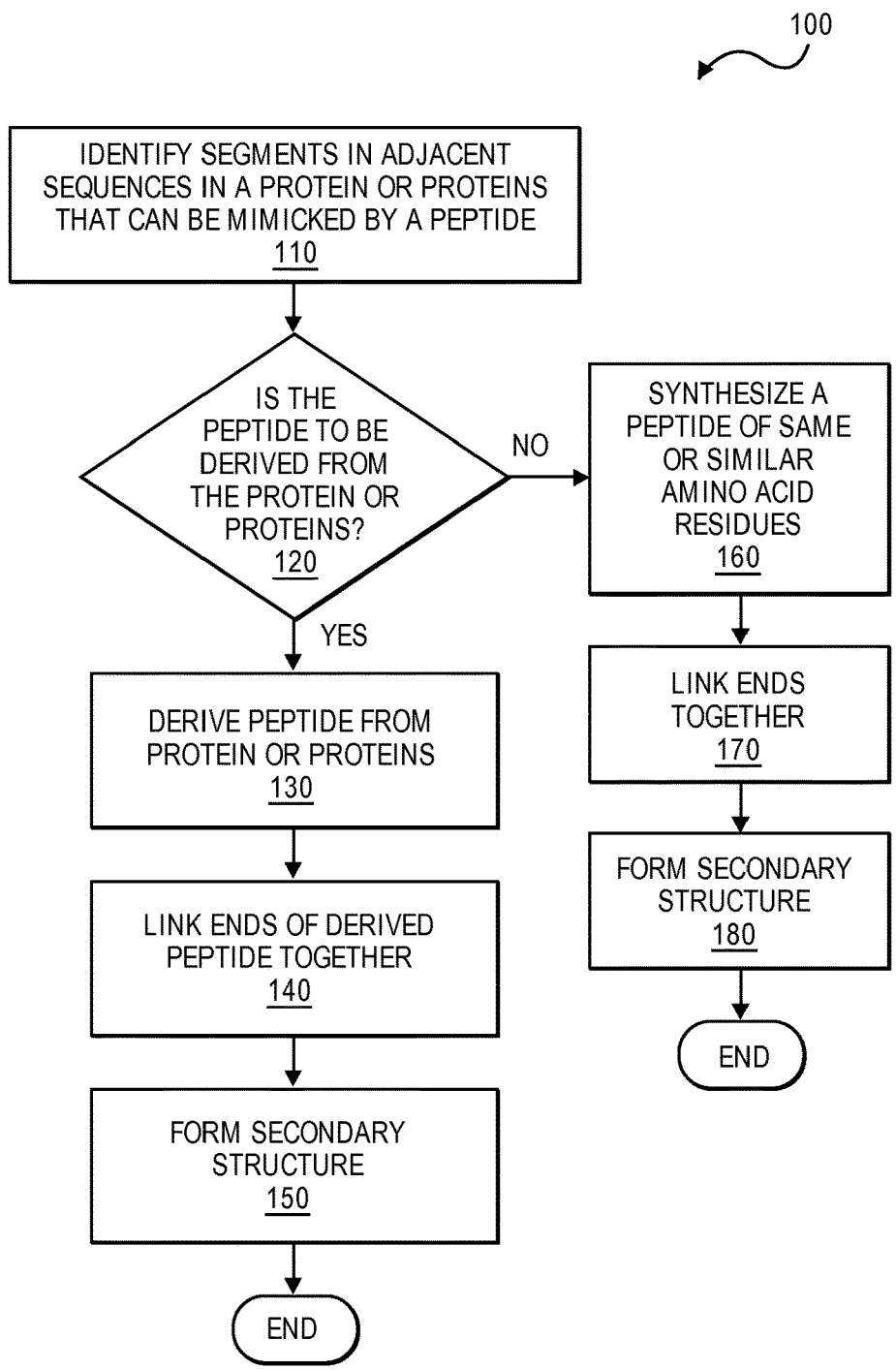
FIG. 1 is a flow chart of an embodiment of a method forming a peptide that mimics the structure of a protein or proteins.

FIG. 1 is a flow chart of an embodiment of a method or methods of forming peptides that mimic a segment in proteins or in adjacent proteins (e.g., adjacent proteins of a protein complex). In one embodiment, the method may be implemented in non-transitory, machine-readable instructions capable and intended to be executed by a computer or processor.

For many proteins and protein complexes, a three dimensional structure is known in the art or can be well modeled. For many structures, there are adjacent short stretches of antiparallel and nearly antiparallel sequences, often in exposed loop regions, particularly at the end of beta-sheet like secondary structures (β hairpins), though such arrangements of short sequences may be found many other places, including at contact points of different sequences due to tertiary or quaternary protein structure. Other secondary structures that can contain segments of adjacent short stretches of sequences include helices (e.g., a-helix generally contains 3.6 amino acid residues per helix turn). Adjacent sequences, in one embodiment, are sequences separated by a distance of 10 angstroms (Å) or less and, in another embodiment, 6 Å or less and, in another embodiment, a distance that can be bridged by a linker of five amino acid residues or less.

Referring to FIG. 1, method 100 begins by identifying segments in adjacent sequences in a protein or proteins that can be mimicked by a peptide (block 110). In one embodiment, protein structures (e.g., protein structures contained in the Protein Data Bank (PDB)) are scanned using one or more predetermined constraints. In one embodiment, protein structures are scanned (e.g., four to seven amino acid residues) for motifs of short stretches, scanning in frame and excerpting from the structure, for example, antiparallel pairs or triplets, etc. of short subsequences (e.g., four to seven amino acid residues) whose ends are constrained to be within a certain predetermined distance, typically that which can be bridged by an amino acid linker, such as an amino acid linker of less than five amino acid residues (e.g., a two, three or four amino acid linker region) without strain.

The concept for the function of these sequences is that a linear peptide composed of the two linked subsequences is flexible and can replicate a secondary structure (e.g., fold or jack-knife) so that the two subsequences, synthesized as part of a unidirectional linear peptide, can take on an antiparallel orientation similar to that of the protein structure that is being mimicked. To mimic a secondary structure of a protein that runs sequence parallel, an amino acid linker can incorporate a synthetic chemical element such as a cross-linker to join the parallel subsequences in, for example, a branched rather than a linear strand.

Once the spatially adjacent segments in the sequences in a protein or proteins are identified, a peptide that mimics the identified segment(s) may be assembled. In one embodiment of a method, a query is whether the peptide is to be derived from the protein or proteins (block 120). Where the peptide is to be derived from the protein or proteins, the peptide may be derived by, for example, removing the subsequences of each spatially adjacent sequence that make up the identified sequence from the actual protein(s) (block 130). In the embodiment where a part of the identified structure is adjacent to a β hairpin, the subsequences may be derived from the protein or the subsequences and the loop portion (e.g., consisting of a few amino acid residues) may be derived from the protein. In other words, the derived peptide may include only the subsequences from the protein or the subsequences and the amino acid residues that make up the loop portion. At this point, to the extent that the ends of the subsequences are not connected (e.g., the amino acid residues that make up the loop portion are not removed from the protein with the subsequences), the ends of each subsequence may be connected such as by attaching peptide linkers of, for example, less than five amino acid residues to the C- and N-termini adjacent subsequences, respectively, for an anti-parallel configuration (block 140).

Following the linking of the end of the derived peptide, the peptide may be formed into a secondary structure with an orientation similar to the protein from which the peptide was derived (block 150). To maintain the secondary structure form, one or more cross-linkers may be added to the structure. One strategy is to incorporate two cysteine residues in locations that become opposing after the peptide "jackknifes". These residues may then form a disulfide bridge or cross-link by reaction of the side-chain sulfhydryls under oxidizing conditions.

There are a range of chemistries well understood in the art of protein chemists for post-synthesis cross-linking two natural amino acid side chains, based on linking together two reactive groups that react specifically with certain side chains. Generally these are either homobifunctional (e.g., lysine-lysine crosslinking with a chemical that looks like N-hydroxysuccinimide ester—linker backbone-N-hydroxysuccinimide ester) or heterobifunctional (e.g., lysine-cysteine cross-linking with NHS ester—linker-maleimide).

Because non-natural amino acids can be incorporated in synthetic peptides, the peptide can be synthesized with a reactive side chain that is capped, and then the cap removed after the linear chain is formed, or other cross-linking reaction schemes can be used.

In above embodiment, the peptide was derived from the protein or proteins that was/were evaluated. In another embodiment, a peptide that mimics identified segments in adjacent sequences in a protein or proteins may be synthesized (block 160). Such synthesis may include synthesizing a peptide having subsequences identical to that of a protein or proteins from which the structure was identified. Alternatively, such synthesis may involve substituting one or more amino acid residues in a subsequence for another amino acid residue or chemical structure of similar or a different property. For example, if a rigidity of a secondary structure of a peptide is a concern, a more rigid amino acid residue or molecule may be substituted for an amino acid residue that might be present in the natural peptide. Generally, substitutions are made on the basis of rational design (e.g., substitute a less bulky side chain for a bulky side chain to relieve steric barriers observed in the native crystal structure, reactive side chains such as cysteine may be substituted by threonine which is nonreactive) or as part of random optimization such as the peptide is put onto a phage display library with random sequence mutations and screened for improved binding. Following the synthesis of the peptide, the end of a peptide may be linked together (block 170) and a secondary structure formed (block 180).

Peptides formed according to the above method may be used in a variety of platforms. Such platforms may include peptide array systems or display systems (e.g., bacteriophage, virus-like) in which the peptides are, for example, cross-linked to the systems and solid state supports with peptides synthesized thereon.

Figure 2:
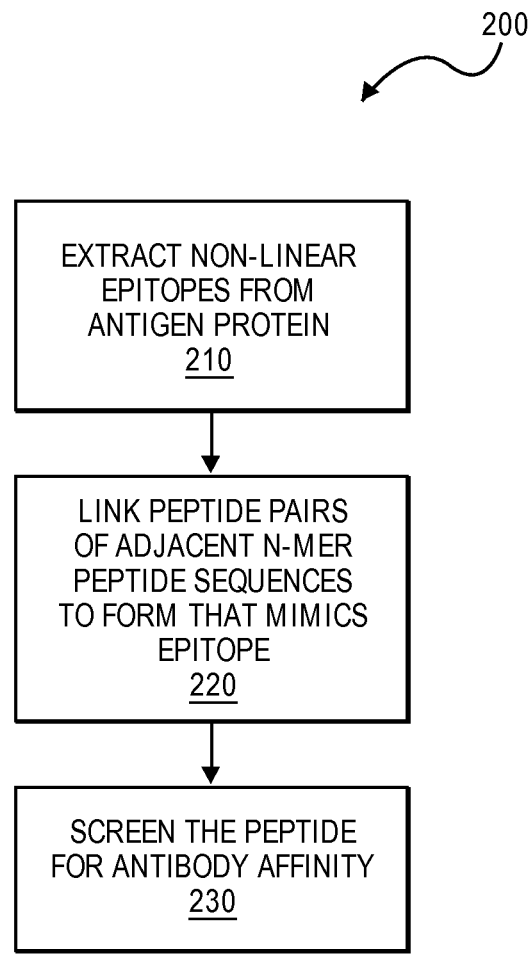
FIG. 2 is a flow chart of an embodiment of forming a peptide that mimics an epitope of a protein.

FIG. 2 is a flow chart of a method of forming peptides that mimic structural epitopes. Similar to the above method, the method of forming peptides that mimic structural epitopes may be implemented in non-transitory, machine-readable instructions operable to be executed by a computer or processor.

For many antigen proteins and protein complexes, a three dimensional structure is known in the art or can be well modeled. For many of these structures, it is found that there are adjacent short stretches of antiparallel or nearly antiparallel sequence, often in exposed loop (β hairpin) regions, particularly at the ends of beta-sheet like secondary structures, though such arrangements of short sequence stretches may be found many other places, including at contact points of different sequences due to tertiary or quaternary protein structure. These motifs include structural epitopes, spatially adjacent, discontiguous subsequences that may be recognized by a particular Ab.

Referring to FIG. 2, in one embodiment, method 200 begins by extracting potential non-linear epitopes (e.g., all of the potential epitopes) on a surface of an antigen protein (block 210). Given a protein database (PDB) structure of a candidate antigen protein, in one embodiment, the method searches the surface of the protein for pairs of discontiguous n-mer peptide sequences, where the length n of the n-mer sequences and the number of amino acids occurring in the intervening sequence space between the two sequences are user-specified. In addition, a user can have control over a geometric orientation of the two n-mer peptide sequences in each pair, including the extent to which they are parallel/antiparallel and a physical distance between the C- and N-termini of the first and second peptides. Once the complete ensemble of all possible n-mer peptide pairs has been generated, the peptide pairs can be linked together as part of a single molecule by attaching peptide linkers of appropriate length to the C- and N-termini of the first and second subsequences, respectively (block 220). With this methodology, large panels of simplified epitope peptides ("epitope patcher") can be quickly designed for antibody screening experiments. The peptide can thus present to an Ab that binds to the epitope patch from which the sequences have been excerpted. Alternatively, an Ab that binds one subsequence, may subsequently bind the second after sufficient conformations are sampled, in either case increasing the affinity or avidity of the binding interaction.

Structural epitope peptides designed using this procedure have been synthesized and employed as part of peptide arrays. Some of these peptides taken from flaviviral envelope proteins have been found to have good t-scores for differentiating between West Nile and Dengue Flavivirus.

Figure 3:
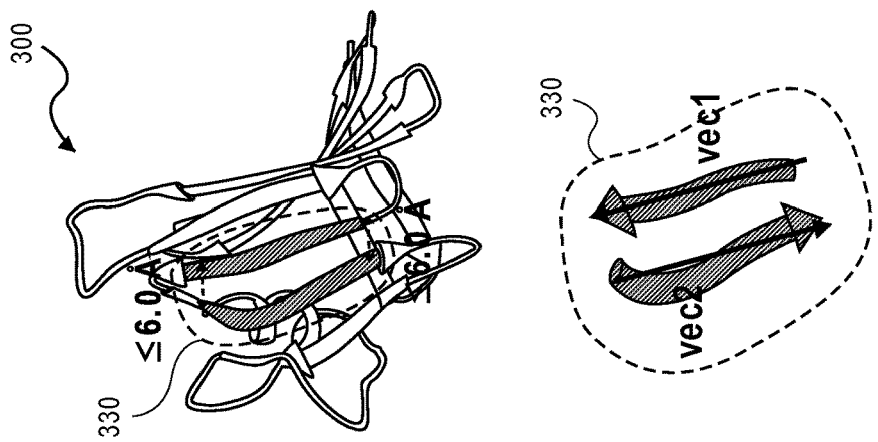
FIG. 3 shows an identification of spatially adjacent subsequences in a protein according to a constraint of strand vectors forming an angle greater than 90° C. and a distance between subsequences of ≤6.0 Å from the C-terminus of strand 1 to the N-terminus of strand 2.
Figure 4:
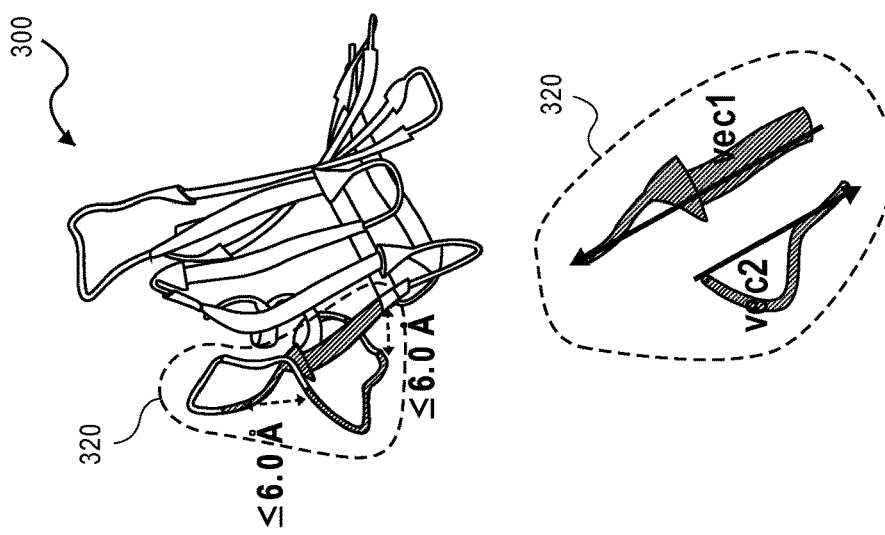
FIG. 4 shows adjacent subsequences in the same protein as FIG. 3 but according to a constraint of a strand vectors forming an angle greater than 150° and a distance between subsequences of ≤6.0 Å from the C-terminus of strand 1 to the N-terminus of strand 2.
Figure 5:
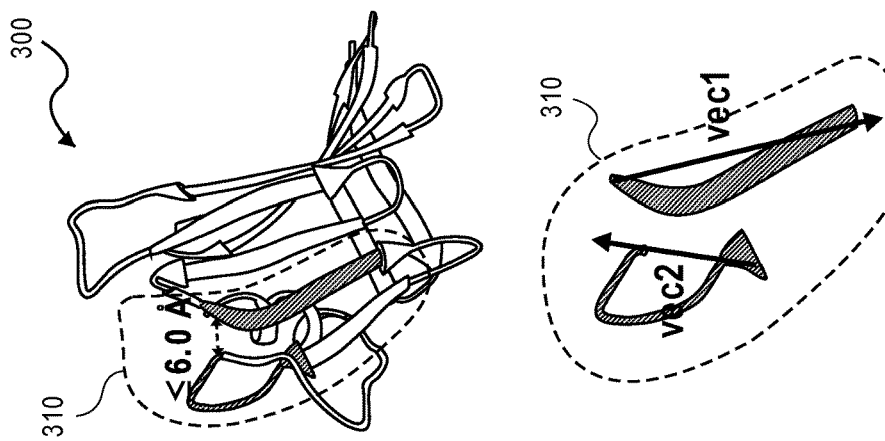
FIG. 5 shows adjacent subsequences in the same protein as in FIGS. 3 and 4 but according to a constraint of a strand vectors forming an angle greater than 150° and a distance between the N-terminus of strand 1 and the C-terminus of strand 2 being ≤6.0 Å.

FIGS. 3-4 show various ways of expressing antiparallel strands using different constraints to identify subsequences in a protein for forming peptides according to a method such as described above. FIG. 3 shows adjacent subsequences 310 of protein 300 according to a constraint of strand vectors forming an angle greater than 90° C. and a distance between subsequences of ≤6.0 Å from the C-terminus of strand 1 to the N-terminus of strand 2. FIG. 4 shows adjacent subsequences 320 of protein 300 according to a constraint of a strand vectors forming an angle greater than 150° and a distance between subsequences of ≤6.0 Å from the C-terminus of strand 1 to the N-terminus of strand 2. FIG. 5 shows adjacent subsequences 330 of protein 300 according to a constraint of a strand vectors forming an angle greater than 150° and a distance between the N-terminus of strand 1 and the C-terminus of strand 2 being ≤6.0 Å. The identified and isolated pairs of subsequences in each of FIGS. 3-4 may be linked together, in one embodiment, either at the top or bottom (as viewed) and may be cross-linked at one or more other locations.

Figure 6:
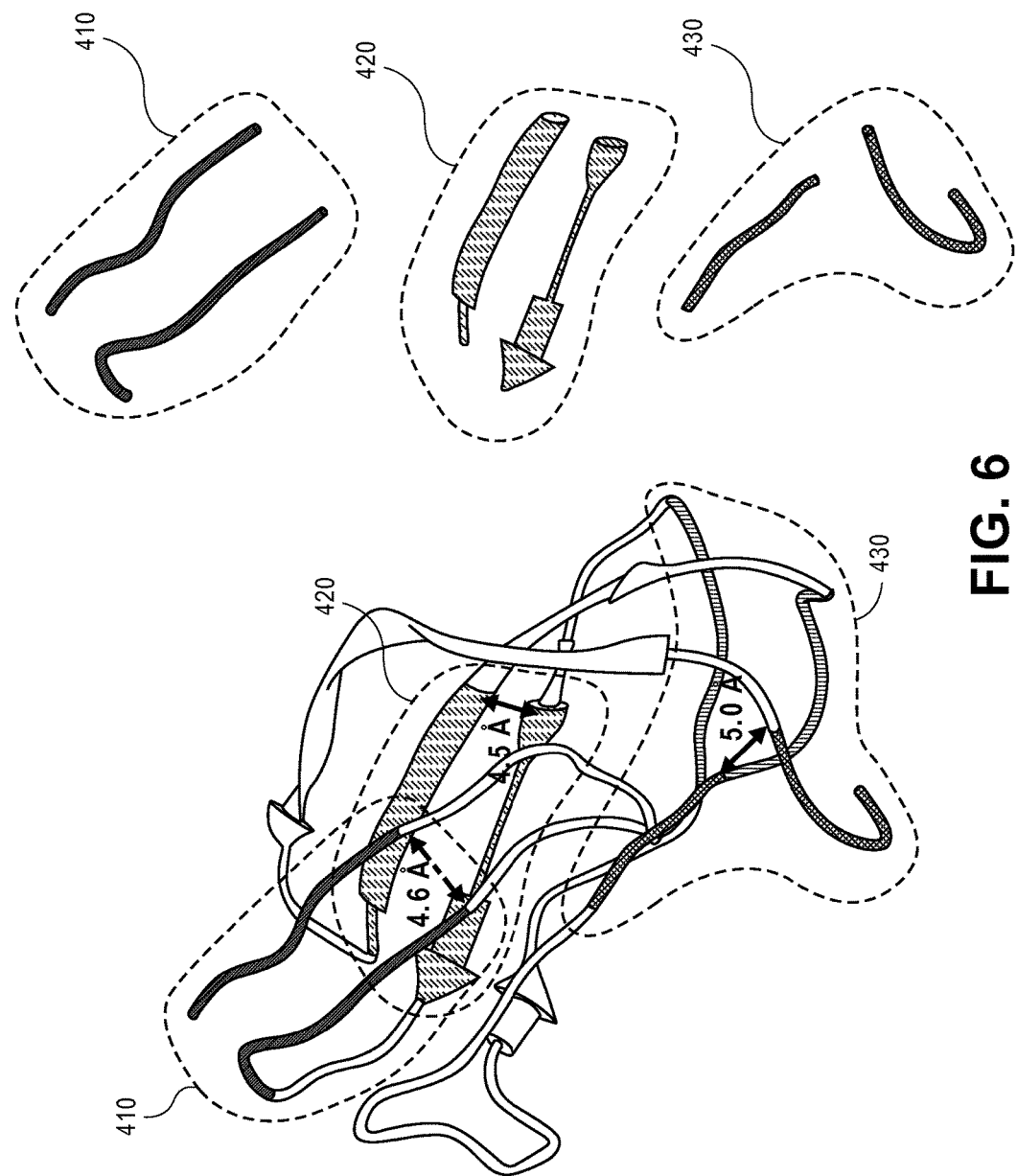
FIG. 6 shows a representation of Dengue Envelope Protein E and identified adjacent subsequences in the protein.

FIG. 6 shows Dengue Envelope Protein E 400 and the identification of adjacent subsequences 410, 420 and 430.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated in the figure to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description, various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
   identifying a non-linear epitope comprising one or more secondary structures in spatially adjacent discontiguous first and second subsequences of one or more proteins that can be mimicked by a synthesized peptide, wherein the first and second subsequences that define the peptide mimic include two to less than 10 amino acid residues, wherein the secondary structures in the spatially adjacent first and second subsequences are separated by a distance of 10 angstroms or less;
   assembling a peptide that mimics the one or more secondary structures, wherein the secondary structures are stabilized using at least one covalent modification, wherein the secondary structures are linked together as part of a single synthesized peptide molecule by attaching peptide linkers to the C- and N-termini of the first and second subsequences and cross-linking the first and second subsequences, wherein the assembled peptide has less than 20 amino acid residues, and wherein the assembled peptide presents one or more binding sites to an antibody that binds to the epitope from which the subsequences have been excerpted; and
   assaying a sample solution using the peptide to identify a presence of the one or more proteins that the peptide mimics in the sample solution.

2. The method of claim 1, wherein the adjacent sequences are part of the same protein.

3. The method of claim 1, wherein the peptide comprises a pair of subsequences of less than 10 amino acids from each of the adjacent sequences.

4. The method of claim 3, wherein assembling comprises connecting the subsequences with a linker of less than five amino acids.

5. The method of claim 1, wherein the one or more secondary structures are selected from the group consisting of a helix and a β hairpin.

6. A method comprising:
   assembling epitopes of linked pairs of discontiguous peptide subsequences that mimic one or more structures in sequences of a protein,
   wherein the subsequences that define the peptide mimic include two to less than 10 amino acid residues,
   wherein the synthesized peptide has less than 20 amino acid residues,
   wherein the linked pairs of discontiguous peptide subsequences are linked together as part of a single molecule by attaching peptide linkers to a C-termini and an N-termini of ones of the subsequences,
   wherein the linked pairs of discontiguous peptide subsequences are formed into a secondary structure maintained by a cross-linker,
   wherein the secondary structures are stabilized using at least one covalent modification, and
   wherein the synthesized peptide presents one or more binding sites to antibodies that bind to each of the epitopes from which the subsequences have been excerpted; and
   assaying antibodies against the epitopes to identify a presence of the antibodies in a solution.

7. The method of claim 6, wherein each of the linked pairs of subsequences are less than 10 amino acids.

8. The method of claim 6, wherein the one or more structures are selected from the group consisting of a helix and a β hairpin.

9. The method of claim 6, wherein assembling comprises linking pairs of discontiguous subsequences with a linker of less than five amino acids.

* * * * *